US008715726B2

(12) United States Patent
Junior et al.

(10) Patent No.: US 8,715,726 B2
(45) Date of Patent: May 6, 2014

(54) PHARMACEUTICAL COMPOSITION COMPRISING TRAMADOL AND KETOPROFEN IN ASSOCIATION

(75) Inventors: Dante Alario Junior, São Paulo (BR); Henry Jun Suzuki, São Paulo (BR)

(73) Assignee: Eurofarma Laboratories S.A., Sao Paulo-SP (BR)

( * ) Notice: Subject to any disclaimer, the term of this patent is extended or adjusted under 35 U.S.C. 154(b) by 410 days.

(21) Appl. No.: 12/525,035

(22) PCT Filed: Jan. 28, 2008

(86) PCT No.: PCT/BR2008/000024
§ 371 (c)(1),
(2), (4) Date: Nov. 16, 2009

(87) PCT Pub. No.: WO2008/092219
PCT Pub. Date: Aug. 7, 2008

(65) Prior Publication Data
US 2010/0062060 A1    Mar. 11, 2010

(30) Foreign Application Priority Data
Jan. 29, 2007  (BR) .................................... 0700133

(51) Int. Cl.
*A61K 9/20*       (2006.01)

(52) U.S. Cl.
USPC ........................... 424/465; 424/451; 424/464

(58) Field of Classification Search
None
See application file for complete search history.

(56) References Cited

U.S. PATENT DOCUMENTS

| 5,914,129    | A  * | 6/1999 | Mauskop ..................... 424/464 |
| 7,332,183    | B2 * | 2/2008 | Plachetka et al. ............. 424/472 |
| 2005/0074493 | A1 * | 4/2005 | Mehta et al. ................. 424/469 |

* cited by examiner

*Primary Examiner* — Anand Desai
*Assistant Examiner* — Melissa Mercier
(74) *Attorney, Agent, or Firm* — Arent Fox LLP

(57) ABSTRACT

The present invention relates to a pharmaceutical composition comprising a combination of active principles. More specifically: a stable pharmaceutical composition comprising a combination of tramadol and ketoprofen. Furthermore, a combination in solid form in which the active principles are vehicled in pharmaceutical forms and/or products that prevent contact between them. Complementarily, the present invention also relates to the combined use of ketoprofen and tramadol in the preparation of an oral medicine useful for relieving pain as well as a method for relieving pain with an oral pharmaceutical composition comprising a combination of tramadol and ketoprofen.

1 Claim, 1 Drawing Sheet

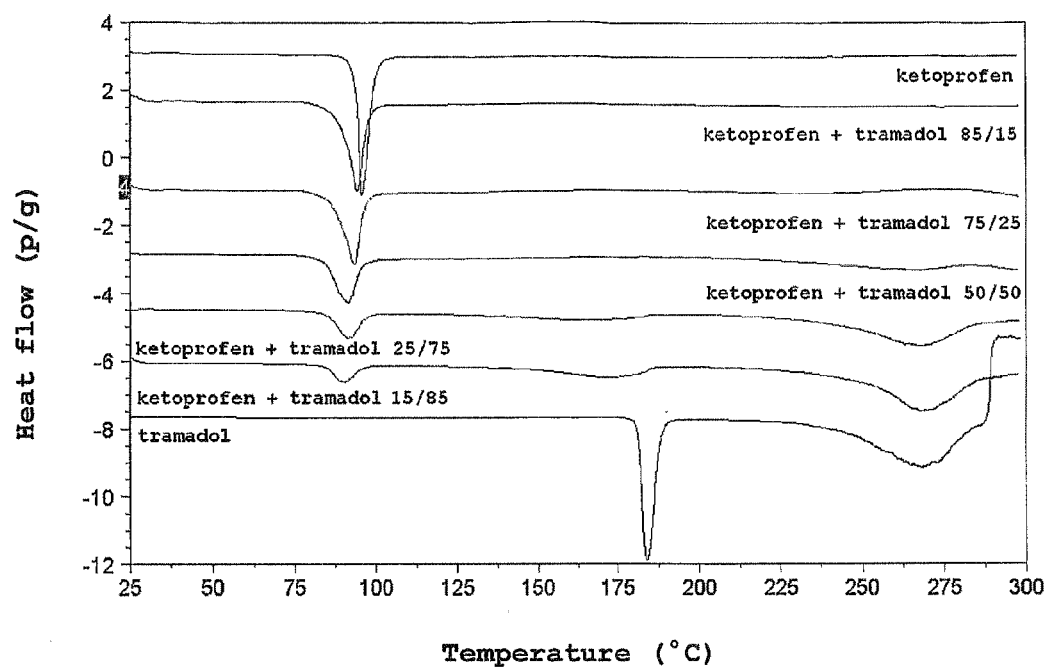

PHARMACEUTICAL COMPOSITION COMPRISING TRAMADOL AND KETOPROFEN IN ASSOCIATION

CROSS-REFERENCE TO RELATED APPLICATION

This application is a National Stage entry of International Application No. PCT/BR2008/000024, filed Jan. 28, 2008, which claims priority to Brazil Patent Application No. PI0700133-9, filed Jan. 29, 2007. The disclosure of the prior application is hereby incorporated in its entirety by reference.

FIELD OF THE INVENTION

The present invention relates to a pharmaceutical composition comprising a combination of active principles. More specifically: a stable pharmaceutical composition comprising a combination of tramadol and ketoprofen. Furthermore, a combination in solid form in which the active principles are vehicled in pharmaceutical forms and/or products that prevent contact between them. Complementarily, the present invention also relates to the combined use of ketoprofen and tramadol in the preparation of an oral medicine useful for relieving pain as well as a method for relieving pain with an oral pharmaceutical composition comprising a combination of tramadol and ketoprofen.

BACKGROUND OF THE INVENTION

Tramadol, with the chemical name of 2-((dimethylamino)methyl)-1-(m-methoxyphenyl)-cyclohexanol (CAS RN: 27203-92-5), is an opioid analgesic agent used in the symptomatic treatment of moderate to severe neuropathic pains. The usual dose of tramadol (normally vehicled in the form of a hydrochloride salt) consists of two daily 50 mg doses, but may attain 400 mg daily. Tramadol is first eliminated hepatically. After oral administration, tramadol is extensively metabolised in the liver. Approximately 30% of the dose administered orally is excreted in the urine not having been metabolised while 60% of the dose is excreted in the form of metabolites.

Ketoprofen, with the chemical name of 2-(3-benzoylphenyl) propionic acid (CAS RN: 22071-15-4) is a non-steroid anti-inflammatory agent (NSAI) having remarkable analgesic, anti-inflammatory, antipyretic and anti-rheumatic properties. The usual posology for ketoprofen, which is normally vehicled in acid form, is of two daily 100 mg doses or three daily 50 mg doses. The exact metabolism of ketoprofen is unknown but, however, it has been ascertained that it is also extensively metabolised in the liver.

Despite interacting with a large number of drugs, tramadol is successfully used in certain combinations, with the notable existence of a commercial product containing a combination of tramadol and paracetamol (Ultracet®, Janssen Cilag).

Data from experiments relating to potential synergic effect of tramadol with specific NSAIs where provided in U.S. Pat. No. 5,516,803 (tramadol in combination with ibuprofen) and in a communication dated Aug. 12, 2000, referring to the publication of EP546676 A1 tramadol in combination with NSAIs, especially ibuprofen). Furthermore, the combined use of tramadol and ketoprofen, in injectable form, was described by Siyam et al. (Co-Administration of Tramadol and Ketoprofen Produces Marked Antinociceptive Synergy with Reduced Side-Effects, Anesthesiology 2003; 99: A996) and by Tuncer et al. (Adding ketoprofen to intravenous patient-controlled analgesia with tramadol after major gynecological cancer surgery: a double-blinded, randomized, placebo-controlled clinical trial, Eur J Gynaecol Oncol. 2003; 24(2):181-4), although it should be stressed that these publications do not contain experimental data that ascertain the existence of synergism with tramadol and ketoprofen when these drugs are administered orally.

With the intent of obtaining a product with an optimal efficiency and safety profile as well as greater ease of administration, the inventors herein ascertained that a combination of tramadol with ketoprofen administered orally could be especially interesting due to the high analgesic potential of tramadol associated with the anti-inflammatory and analgesic properties of ketoprofen.

However, it proved that physical-chemical interaction occurred in formulations where the active principles came into contact which resulted in the formation of a thick viscous mass hard to dissolve that could result in an alteration of the bioavailability of the drugs.

With the objective of resolving the problem of interaction and maintaining the bioavailability of the drugs unaltered when these are vehicled in solid pharmaceutical forms, the inventors herein ascertained that is was especially interesting to vehicle tramadol and ketoprofen in pharmaceutical forms and/or products that prevent contact between them and/or impede interaction between the two active principles.

To the best knowledge of the inventors herein, there does not exist in the current state-of-the-art any publication concerning the efficiency and safety of an oral administration of a pharmaceutical composition comprising a specific combination of tramadol and ketoprofen, or the physical-chemical interaction between such active principles when vehicled in pharmaceutical forms and/or products that provide contact between them.

BRIEF DESCRIPTION OF THE DIAGRAM

FIG. 1: Thermoanalytic curves from differential scan calorimetry (DSC) of the tramadol hydrochloride and ketoprofen, both isolated and combined in different proportions.

DESCRIPTION OF THE INVENTION

In a first aspect, the present invention comprises a pharmaceutical composition to be administered orally comprising a combination of tramadol, ketoprofen and, optionally, one or more pharmaceutically acceptable excipients.

In accordance with the present invention, the term combination comprises products in which tramadol and ketoprofen are included in a single unit of dosage (i.e. a single tablet or capsule), as well as in the form of kits for the joint administration of the drugs (i.e. blister type packaging combining tramadol tablets and ketoprofen tablets or sets of vials containing tramadol tablets and vials containing ketoprofen tablets).

In accordance with the present invention, the term tramadol shall be considered as being tramadol in its base free form, as well as tramadol salts or solvates of these. In a preferred embodiment, tramadol shall be in the form of its hydrochloride salt.

In accordance with the present invention, the term ketoprofen shall be considered as being ketoprofen in acid form, as well as ketoprofen salts with organic or inorganic bases and the hydrates or solvates of these. In a preferred embodiment, ketoprofen shall be in its acid form.

Examples of pharmaceutically acceptable excipients include those described in the publication: *Remington's Pharmaceutical Sciences*, 17$^{th}$ ed., Mack Publishing Company, Easton, Pa., USA.

In a second aspect, the present invention comprises a solid pharmaceutical composition in which tramadol and ketoprofen are vehicled in pharmaceutical forms and/or products that prevent contact between the two active principles, since the physical-chemical interaction between tramadol and ketoprofen leads to the formation of an eutectic mixture, as can be seen from the tests with differential scan calorimetry (DSC) (FIG. 1).

Examples of pharmaceutical forms that prevent contact between the two active principles are: triple layered tablets in which each active principle is placed in a separate layer with at least one intermediate barrier layer; capsules containing tramadol based granulates and ketoprofen based granulates maintained separate and, more specifically, coated; capsules and/or tablets comprising coated ketoprofen crystals and coated tramadol crystals; capsules containing tramadol tablets and ketoprofen tablets maintained separate and, more specifically, coated.

Examples of pharmaceutical products that prevent contact between the two active principles are: blister type packaging containing tramadol tablets and ketoprofen tablets maintained separate; sets of vials containing ketoprofen capsules and vials containing tramadol capsules; sets of vial-ampoules containing ampoules of tramadol and ampoules of ketoprofen, in solid form, maintained separate.

The present invention is not limited to the type of release of the active principles and includes products with immediate release, controlled release, timed release, rapid disintegration, etc.

The present invention relates to combinations of ketoprofen and tramadol in pharmaceutically acceptable doses. In accordance with an illustrative aspect but without, however, limiting the range of the scope of the present invention, these doses include but are not limited to 50 mg doses of tramadol at each administration and 50 mg doses of ketoprofen at each administration.

In a third aspect, the present invention comprises the combined use of tramadol and ketoprofen in the preparation of a medicine for relieving pain.

In a fourth aspect, the present invention relates to a method for relieving pain comprising the combined administration of tramadol and ketoprofen. Examples of possible pains liable to treatment include, but are not limited to: toothache, headache (cephalalgia), migraine, abdominal and pelvic pains, rheumatic pains, neuralgia, fever pains, influenza and common cold symptoms, sore throats, lumbalgia, muscular pains (myalgia), wryneck (torticollis), articular pains, leg pains, contusions, sprains, tendinitis, tennis elbow, lumbago, arthralgia, post-traumatic pain, sciatica, bursitis, distentions, minor phlebitis, painful conditions of the spinal column (spinalgia), minor sport injuries, varicose pains, varicose inflammations, bruising (haematomas), intense pains of an acute, subacute and chronic nature (postoperative, tumours, myocardial infarction, traumatisms, fractures) and acute pains from diagnostic and therapeutic measures.

In accordance with a preferential aspect, the present invention comprises the simultaneous administration of tramadol and ketoprofen or the separate administration of ketoprofen and tramadol but at a time interval of less than 60 minutes between each dose of drug.

Detailed descriptions of examples of formulations and experimental examples are provided below and illustrate the present invention without, however, serving to limit its scope.

EXAMPLES

Example 1

Production of 50 mg Tramadol Tablets

Batch size: 4.000 tablets

| Tablet nucleus: | |
|---|---|
| (a) Tramadol hydrochloride | 200 g |
| (b) Microcrystalline cellulose | 240 g |
| (c) Monohydrated lactose | 352 g |
| (d) Magnesium stearate | 8 g |

Sieve ingredients (a), (b) and (c) through 40 mesh. Transfer powder to a mixer-granulator and mix for 5 minutes.

Sieve ingredient (d) through 60 mesh and mix for 3 minutes.

The resulting final mixture was compressed using 11×6.5 mm punches into oblong tablets having the following characteristics: average weight: 200 mg; size: 11×6.5 mm; hardness: 5 to 12.0 kPa; tablet humidity at 105° C./10 min: maximum of 6%; friability: maximum of 1%.

Production of Coated Tablet:

| Coating suspension: | |
|---|---|
| (e) Hypromelose/macrogol | 20 g |
| (f) Titanium dioxide | 3.6 g |
| (g) Blue lac dye | 0.4 g |
| (h) Distilled water | 250 mL |

Add (e) to an adequate vessel containing 200 mL of (h), under constant agitation until the solution becomes transparent (I).

Prepare the pigment suspension by adding (f) and (g) in an adequate vessel containing 50 mL of (h), and homogenise with an agitator for 3 minutes (II).

Mix (I) and (II) under gentle agitation until a homogenous suspension is formed (coating suspension).

Apply the coating suspension over the tablet nuclei by aspersion in appropriate coating equipment having forced air circulation.

Average weight of tablet nucleus: 200 mg; Average weight of tablet with coating: 206 mg.

Example 2

Production of 50 mg Ketoprofen Tablets

Batch size: 4.000 tablets

| Tablet nucleus: | |
|---|---|
| (a) Tramadol hydrochloride | 200 g |
| (b) Monohydrated lactose | 560 g |
| (c) Dibasic calcium phosphate | 32 g |
| (d) Magnesium stearate | 8 g |

Sieve ingredients (a), (b) and (c) through 40 mesh. Transfer powder to a mixer-granulator and mix for 5 minutes.

Sieve ingredient (d) through 60 mesh and mix for 3 minutes.

The resulting final mixture was compressed using 11×6.5 mm punches into oblong tablets having the following characteristics: average weight: 200 mg; size: 11×6.5 mm; hardness: 5 to 12.0 kPa; tablet humidity at 105° C./10 min: maximum of 6%; friableness: maximum of 1%.

Production of Coated Tablet:

| Coating suspension: | |
|---|---|
| (e) Hypromelose/macrogol | 20.4 g |
| (f) Titanium dioxide | 3.6 g |
| (g) Distilled water | 250 mL |

Add (e) to an adequate vessel containing 200 mL, of (g), under constant agitation until the solution becomes transparent (I).

Prepare the pigment suspension by adding (f) to an adequate vessel containing 50 mL of (g), and homogenise with an agitator for 3 minutes (II).

Mix (I) and (II) under gentle agitation until a homogenous suspension is formed (coating suspension).

Apply the coating suspension over the tablet nuclei by aspersion in appropriate coating equipment having forced air circulation.

Average weight of tablet nucleus: 200 mg; Average weight of tablet with coating: 206 mg.

Example 3

Kit Containing Tramadol Tablets and Ketoprofen Tablets in a Single Blister

A 50 mg tramadol tablet (Example 1) and a 50 mg ketoprofen tablet (Example 2) were enclosed in double bubble PVDC blister. After sealing with aluminium laminate, 14 such blisters were packed in a cardboard carton together with instructions for administering the contents of a blister every 12 hours.

Example 4

Kit Containing Tramadol Tablets and Ketoprofen Tablets in Blister Packs

Two 50 mg tramadol tablets (Example 1) were enclosed in double bubble blister. Two 50 mg ketoprofen tablets (Example 2) were enclosed in double bubble blister. After sealing with aluminium laminate, each of the two blisters were then bonded to a light cardboard backing having two rows of two holes each aligned in such a manner as to allow insertion of the blisters to form two rows of blister enclosed tablets with the bubbles being exposed through the holes with each row thus being composed of single tramadol tablets and single ketoprofen tablets. Five such packs were packaged in a cardboard carton together with instructions for administering the contents of a two tablet row consisting of a tramadol tablet and a ketoprofen tablet at each prescribed dose.

Example 5

Production of Capsules Containing a Tramadol Based Tablet and a Ketoprofen Based Tablet A 50 mg tramadol tablet (Example 1) and a 50 mg ketoprofen tablet (Example 2) were enclosed in a zero size gelatin capsule.

Example 6

Production of 50 mg Ketoprofen Granulated Powder

| Production of ketoprofen granulated powder: | |
|---|---|
| (a) Ketoprofen | 500 g |
| (b) Lactose super tab | 480 g |
| (c) Croscarmellose sodium | 10 g |
| (d) Magnesium stearate | 10 g |

Sieve ingredients (a), (b) and (c) through 40 mesh.

Transfer powder to a mixer-granulator and mix for 5 minutes.

Sieve ingredient (d) through 60 mesh, add to granulate and mix for 5 minutes.

Example 7

Production of Capsules Containing Combined but Isolated Tramadol and Ketoprofen Enclose a specifically coated 50 mg tablet of tramadol (Example 1) and 100 mg of granulated ketoprofen (Example 6) in an adequately proportioned capsule of hard gelatin.

Example 8

Production of Capsules Containing Combined Granulated Tramadol and Granulated Ketoprofen without being Isolated Batch amount: 3181 capsules

| Production of granulate to be mixed | |
|---|---|
| (a) Ketoprofen | 160.0 g |
| (b) Tramadol hydrochloride | 160.0 g |
| (c) Monohydratad lactose | 360.0 g |
| (d) Croscarmellose sodium | 14.0 g |
| (e) Magnesium stearate | 7.0 g |

Sieve ingredients (a), (b), (c) and (d) through 25 mesh:

Mix for 5 minutes following which add the previously sieved magnesium stearate and further mix for 2 minutes.

Enclose 220 mg of the mixed granulate in an adequately proportioned capsule of hard gelatin.

Example 9

Comparative Stability Data for the Capsules Containing Combined Tramadol and Ketoprofen without Isolation of the Active Principles and Capsules Containing Combined Tramadol and Ketoprofen with Isolation of the Active Principles Capsules containing combined granulated tramadol and granulated ketoprofen without isolation of the active principles (Example 8) and capsules produced according to example 7 containing a coated tablet of tramadol (Example 1) and granulated ketoprofen (Example 6) were placed in separate hermetically sealed glass vials. The vials were then placed in an oven (temperature of 40° C. and relative humidity of 75%) in compliance with RE1 (2005) of the National Health Surveillance Agency (Anvisa). The capsules were assessed after a period of 30 and 60 days. It was possible to ascertain that after only 30 days a pasty mass that was difficult to dissolve formed on the walls inside the capsules containing the mixture of granulated tramadol and granulated ketoprofen without isolation, while those capsules containing a coated tablet of tramadol and granulated ketoprofen remained practically unaltered.

Example 10

Differential Scan Calorimetry (DSC) Data from the Tramadol Hydrochloride Singly, Ketoprofen Singly and The Combination of Tramadol Hydrochloride with Ketoprofen The interaction between the tramadol hydrochloride and ketoprofen was assessed from DSC tests performed on the active principles singly and combined; it was ascertained that the active principles form an eutectic mixture with the suppression of the peak corresponding to the fusion of tramadol hydrochloride in ratios between 15:85 and 85:15.

FIG. 1 show the DSC curves of the active principles singly and in different proportions. These were obtained using a TA-2920 cell (TA-Instruments®), at temperatures ranging from 10 to 200° C., with a hermetically sealed aluminium capsule, using samples of approximately 3.0 mg, a heating rate of 10° C./min and a dynamic nitrogen atmosphere at a flow of 50 mL/min.

It should be stressed that the present invention is not limited to the description herein but further incorporates all the modifications and adaptations within the spirit and scope of the invention.

Example 11

Evaluation of the Safety and Efficiency of the Combined Use of Tramadol Hydrochloride and Ketoprofen Compared to the Use of these Drugs Singly In order to evaluate the efficiency, safety and tolerance of the combined use of the drugs in the treatment of acute lombalgia over a period of 7 days, a multicentric, phase III, double-blind, randomised clinical trial will be conducted by qualified doctors on 171 assessable patients.

The clinical trial shall evaluate: (a) the efficiency of the combined use of tramadol hydrochloride and ketoprofen in the treatment of acute and subacute lombalgia compared to the drugs used singly; (b) the safety and tolerance of the combined use of tramadol hydrochloride and ketoprofen in the treatment of acute and subacute lombalgia compared to the drugs used singly.

For conducting this clinical trial, the patients shall be selected according to the following criteria: (a) Men and women between 18 and 75 years of age; (b) conditions of acute or subacute lumbar pains lasting up to 45 days, with the pains being constant and increasing following attempts to move responding to painful palpations of the lumbar area with maximum radiation extending to the knees. Patients may include those undergoing first episodes or recurrent pains; (c) evaluation of the Analog Visual Scale (AVS) shall be ≥60 mm of the basal evaluation; and (d) signature of the term of awareness and free consent required by the Ethics Council.

The patients selected shall be divided into 3 groups and shall receive the following treatment: (Group 1) 50 mg tramadol hydrochloride+50 mg ketoprofen; (Group 2) 50 mg tramadol hydrochloride; and (Group 3) 50 mg ketoprofen. The patient shall be advised to take one capsule orally every 8 hours, at meal times or together with some light food, for a total of 9 capsules. Following the first 3 days, the patient shall then be asked to only take the capsules when necessary and according to the pain, not exceeding three capsules per day, with a minimum interval of 8 hours between each dose, until the end of treatment (7 days). Back-up medication shall be 750 mg paracetamol.

In order to verify efficiency, evaluation shall be divided into two visits on the $4^{th}$ and $8^{th}$ days.

The visit on the $4^{th}$ day shall evaluate: (a) the decrease in pain in relation to the basal level (day 1) by AVS; (b) vital signs and a physical evaluation; (c) change in the score of the Roland Morris'Quality-of-Life Questionnaire compared to the basal score (day 1); and (d) overall assessment of the actual patient.

The visit on the $8^{th}$ day shall evaluate: (a) the decrease in pain in relation to the basal level (day 1) by AVS; (b) vital signs and a physical evaluation; (c) the number of days occurred before significant remission of the pain defined as an AVS score ≤10 mm; (d) change in the score of the Roland Morris' Quality-of-Life Questionnaire compared to the basal score (day 1); (e) use of the back-up medication; (f) overall assessment of the patient by the doctor; and (g) overall assessment of the treatment by the actual patient.

In order to verify the safety of the treatment, the following shall be evaluated: (a) the spontaneous report of adverse events; and (b) compliance with the treatment.

The invention claimed is:

1. A pharmaceutical composition for relieving pain, in the form of a hard capsule for oral administration, consisting essentially of a combination of: (a) tramadol, or its salts, in the form of a coated tablet; (b) ketoprofen, or its salts, in the form of a granulated powder; and (c) optionally, one or more pharmaceutically acceptable excipients, wherein the tramadol is not in contact with the ketoprofen.

* * * * *